United States Patent
Roe

(10) Patent No.: US 11,944,563 B2
(45) Date of Patent: Apr. 2, 2024

(54) WEARABLE DEVICE FOR BODY CORRECTION

(71) Applicant: Value & Trust, Daegu (KR)

(72) Inventor: Kyung Suk Roe, Seoul (KR)

(73) Assignee: VALUE & TRUST, Daegu (KR)

( * ) Notice: Subject to any disclaimer, the term of this patent is extended or adjusted under 35 U.S.C. 154(b) by 357 days.

(21) Appl. No.: 17/325,228

(22) Filed: May 20, 2021

(65) Prior Publication Data

US 2022/0370226 A1 Nov. 24, 2022

(51) Int. Cl.
*A61F 5/00* (2006.01)
*A61F 5/02* (2006.01)

(52) U.S. Cl.
CPC .................. *A61F 5/024* (2013.01)

(58) Field of Classification Search
CPC .... A61F 5/024; A61F 5/02; A61F 5/03; A61F 5/026; A61F 5/028
USPC .......................................................... 602/19
See application file for complete search history.

(56) References Cited

U.S. PATENT DOCUMENTS

| | | | | |
|---|---|---|---|---|
| 5,290,307 A | * | 3/1994 | Choy | A61H 39/04 |
| | | | | 606/204 |
| 5,792,085 A | * | 8/1998 | Walters | A61F 5/024 |
| | | | | 606/54 |
| 6,129,689 A | | 10/2000 | Dibello | |
| 2002/0068890 A1 | * | 6/2002 | Schwenn | A61F 5/0193 |
| | | | | 602/5 |
| 2008/0066272 A1 | * | 3/2008 | Hammerslag | A43C 11/14 |
| | | | | 602/5 |
| 2017/0189219 A1 | * | 7/2017 | Jensen | A61F 2/4455 |

FOREIGN PATENT DOCUMENTS

| | | |
|---|---|---|
| CN | 205612600 U | 10/2016 |
| CN | 205903343 U | 1/2017 |
| CN | 209677431 U | 11/2019 |
| CN | 111067686 A | 4/2020 |
| JP | 2019-501311 A | 1/2019 |
| KR | 10-1070973 B | 10/2011 |
| KR | 10-2020-0077094 A | 6/2020 |
| WO | 2018/081097 A1 | 5/2018 |

(Continued)

OTHER PUBLICATIONS

Extended European Search Report dated May 6, 2022 for European Application No. 21207077.5.

(Continued)

*Primary Examiner* — Adam Baker

(57) ABSTRACT

Disclosed herein is a wearable device for body correction, which is capable of adapting a position suitable for pressing a patient's body's curve to be corrected. To this end, the wearable device for body correction includes an outerwear worn on an upper body of a patient, a curve presser disposed on the outerwear and configured to press a curve of the body to be corrected, a strength adjuster disposed on the outerwear, connected to the curve presser by a wire, and configured to adjust a strength of pressure applied by the curve presser by adjusting an amount of winding/unwinding of the wire, and a guide rail disposed on the outerwear and configured to guide vertical sliding of at least one of the curve presser and the strength adjuster.

14 Claims, 11 Drawing Sheets

(56) References Cited

FOREIGN PATENT DOCUMENTS

WO      2018/186553 A1    10/2018
WO      2020-234244 A    11/2020

OTHER PUBLICATIONS

Tschauner C et al: "Skoliosemieder", Medizinisch Orthopadische Technik, Gentner Verlag, Stuttgart, DE, vol. 113, No. 2, May 1, 1993, pp. 125-126, 131, XP000304145, ISSN 0340-5508.
Notice of Allowance dated Oct. 18, 2022 for Japanese Application No. 2021-175792.

* cited by examiner

WEARABLE DEVICE FOR BODY CORRECTION

BACKGROUND

Technical Field

The present disclosure relates to a wearable device for body correction, and more particularly, to a wearable device for body correction, which is worn on a patient's upper body to press and correct a curve and hump of the body to be corrected.

Description of the Related Art

In general, the human spine is composed of bones that maintain a main skeleton from the neck to the coccyx via the back, the waist, and the hips thereof. Specifically, the spine is divided into 7 neck bones (cervical vertebra), 12 breastbones (thoracic vertebra), 5 hucklebones (lumbar vertebra), 5 sacra (sacral vertebra), and 4 tailbones (coccygeal vertebra).

Meanwhile, the spinal cord is present in the spine as nerve fascicles from the brain, which serves to connect the brain as the central nervous system and the peripheral organs as the peripheral nervous system. As such, the spine is a very important part of the human body, and it gives a lot of trouble to life when suffering from spinal diseases.

Representative examples of the spinal diseases include cervical disc herniation, scoliosis, low back pain syndrome, and intervertebral disc herniation.

In particular, the scoliosis is one of the representative spinal deformities, and causes a "curve" of the human spine which means a "laterally bent condition" or a "laterally curved condition".

Such scoliosis occurs frequently while growing up, with about half of the total number of patients with scoliosis in their teens.

Different measures should be taken depending on the degree of scoliosis, but symptoms often worsen due to the lack of awareness of the disease or simple observation.

The purpose of the treatment for scoliosis is to prevent the mild curve of the spine from progressing further, to correct the curve above severity, and to maintain the corrected spine to achieve body balance and improvement in beauty.

If scoliosis is detected early, conservative methods such as wearing an appropriate orthosis may also prevent the progression to a severe curve.

However, conventional orthoses are not effective in responding to deformity in patients with scoliosis, and may not perform successful spinal correction, especially in the case of adolescents whose growth continues.

Furthermore, patients who use uncomfortable orthoses are not motivated enough to wear them, which makes it easy to give up the use of the orthoses.

Korean Patent No. 10-1070973 (Oct. 6, 2011) (hereinafter, referred to as "prior art") discloses a "spinal orthosis". The prior art relates to a spinal orthosis worn by a patient to correct and recover his/her spine for spinal disorders such as spinal curves.

The prior art includes a back plate that is adjustable in length and angle and has inner/outer skins made of functional fibers, and a waistband detachably attached to the back plate and having a pull string adjuster for tightening with a simple operation.

However, the prior art has a very difficult structure for the patient to adjust the spinal orthosis using the pull string adjuster. Hence, it is necessary to seek help from another person when using the spinal orthosis.

Moreover, for some patients, the scoliosis causes a "hump", which is a posterior protruding part of the human body, in addition to the "curve", wherein the curve and the hump are in different positions for each patient. In addition, the prior art may not adjust the position for pressing the curve and the hump.

PATENT DOCUMENT

Korean Patent No. 10-1070973 (Oct. 6, 2011)

SUMMARY

Accordingly, the present disclosure is directed to a wearable device for body correction that substantially obviates one or more problems due to limitations and disadvantages of the related art.

An object of the present disclosure is to provide a wearable device for body correction, which is capable of adapting a position suitable for pressing a patient's body's curve to be corrected.

Another object of the present disclosure is to provide a wearable device for body correction, which enables a patient to easily adjust a degree of strength for applying pressure to his/her curve.

The present disclosure is not limited to the above-mentioned objects, and other objects of the present disclosure can be clearly understood by those skilled in the art to which the present disclosure pertains from the following description.

In accordance with an aspect of the present disclosure, there is provided a wearable device for body correction, which includes an outerwear, a curve presser, a strength adjuster, and a guide rail. The outerwear may be worn on an upper body of a patient. The curve presser may be disposed on the outerwear. The curve presser may press a curve of the body to be corrected. The strength adjuster may be disposed on the outerwear. The strength adjuster may be connected to the curve presser by a wire. The strength adjuster may be configured to adjust a strength of pressure applied by the curve presser by adjusting an amount of winding/unwinding of the wire. The guide rail may be disposed on the outerwear. The guide rail may be configured to guide vertical sliding of at least one of the curve presser and the strength adjuster.

The least one of the curve presser and the strength adjuster may include a body, a support plate, and a rail moving block. The body may define an external appearance of the at least one of the curve presser and the strength adjuster. The support plate may be disposed between the body and the guide rail. The support plate may be coupled to the body. The rail moving block may be coupled to the support plate. The rail moving block may be slidably coupled to the guide rail.

The strength adjuster may further include a dial adjuster. The dial adjuster may be rotatably coupled to the body to adjust the amount of winding/unwinding of the wire.

The support plate may include a first coupling hole and a second coupling hole formed therein. The second coupling hole may extend in a sliding direction of the rail moving block from the first coupling hole. The second coupling hole may have a smaller width in a direction orthogonal to the sliding direction of the rail moving block than the first coupling hole. The rail moving block may be fitted in the first coupling hole and then slid to the second coupling hole for coupling to the support plate.

The rail moving block may include a latching portion, a support portion, and a coupling portion. The latching portion may have a width in a direction orthogonal to the sliding direction of the rail moving block to be less than or equal to the width of the first coupling hole. The latching portion may have a width in a direction orthogonal to the sliding direction of the rail moving block to be larger than the width of the second coupling hole. The latching portion may have one surface coming into contact with an outer surface of the support plate. The support portion may have a width in a direction orthogonal to the sliding direction of the rail moving block to be larger than the width of the first coupling hole and the width of the second coupling hole. The support portion may have one surface facing the one surface of the latching portion. The one surface of the support portion may come into contact with an inner surface of the support plate. The coupling portion may protrude from the other surface of the support portion. The coupling portion may have a guide groove slidably coupled to the guide rail.

The guide rail may include an attachment plate and a guide protrusion. The attachment plate may be coupled on the outerwear. The guide protrusion may be formed on one side of the attachment plate in a direction orthogonal to the sliding direction of the rail moving block. The guide protrusion may be inserted and rotatably disposed in the guide groove.

The guide groove and the guide protrusion may have a circular cross section.

The coupling portion may have an opening formed to be open at one side of the guide groove. The opening may have an opening width smaller than the diameter of the guide groove.

The strength adjuster may further include a holder fixing pin. The holder fixing pin may be used to couple the body and the support plate. The holder fixing pin may have a latching protrusion formed on an outer peripheral surface thereof. The body may have a through-hole formed therein. The support plate may have a boss formed thereon. The boss may be inserted into the through-hole. The holder fixing pin may be inserted into the boss. The boss may have a latching groove formed therein, and the latching protrusion may be latched to the latching groove.

The wearable device for body correction may further include a pelvic band. The pelvic band may be disposed on the outerwear. The pelvic band may be configured to hold a pelvis of the patient when the curve presser presses the curve.

The wearable device for body correction may further include a back reinforcement plate and a hump pad. The back reinforcement plate may be disposed on an inner surface of a back plate of the outerwear. The hump pad may be attached to any position of the back reinforcement plate related to a position where the curve presser presses the curve, so as to press the body.

The wearable device for body correction may further include a flank band. The flank band may be disposed on the outerwear. The flank band may be configured to hold a flank of the patient when the curve presser presses the curve.

The wearable device for body correction may further include a flank pad. The flank pad may be attached to any position of the flank band related to a position where the curve presser presses the curve, so as to press the body.

Each of the hump pad and the flank pad may include a base and a cushion protrusion. The base may be in the form of a plate. The base may be attached to an associated one of the back reinforcement plate and the flank band. The cushion protrusion may protrude from one surface of the base. The cushion protrusion may have a cushion force to press the body. The base may have a metal wire disposed within a rim thereof.

The wearable device for body correction may further include a point band. The point band may be attached to any position of the outerwear. The point band may include a plurality of vertically spaced metal points arranged thereon.

It is to be understood that both the foregoing general description and the following detailed description of the present disclosure are exemplary and explanatory and are intended to provide further explanation of the disclosure as claimed.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF EMBODIMENTS

Hereinafter, a wearable device for body correction according to exemplary embodiments of the present disclosure will be described with reference to the drawings.

Figure 1:
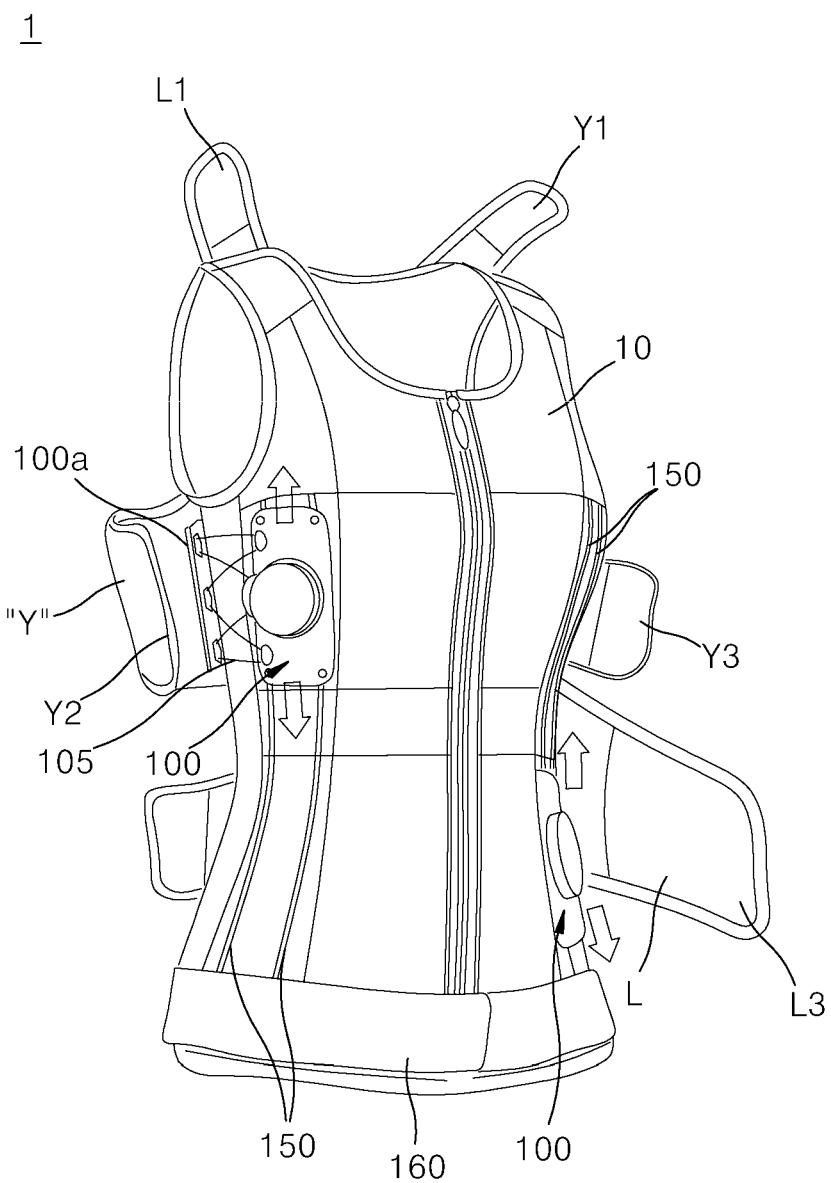
FIG. 1 is a front perspective view illustrating a wearable device for body correction according to an embodiment of the present disclosure.
Figure 2:
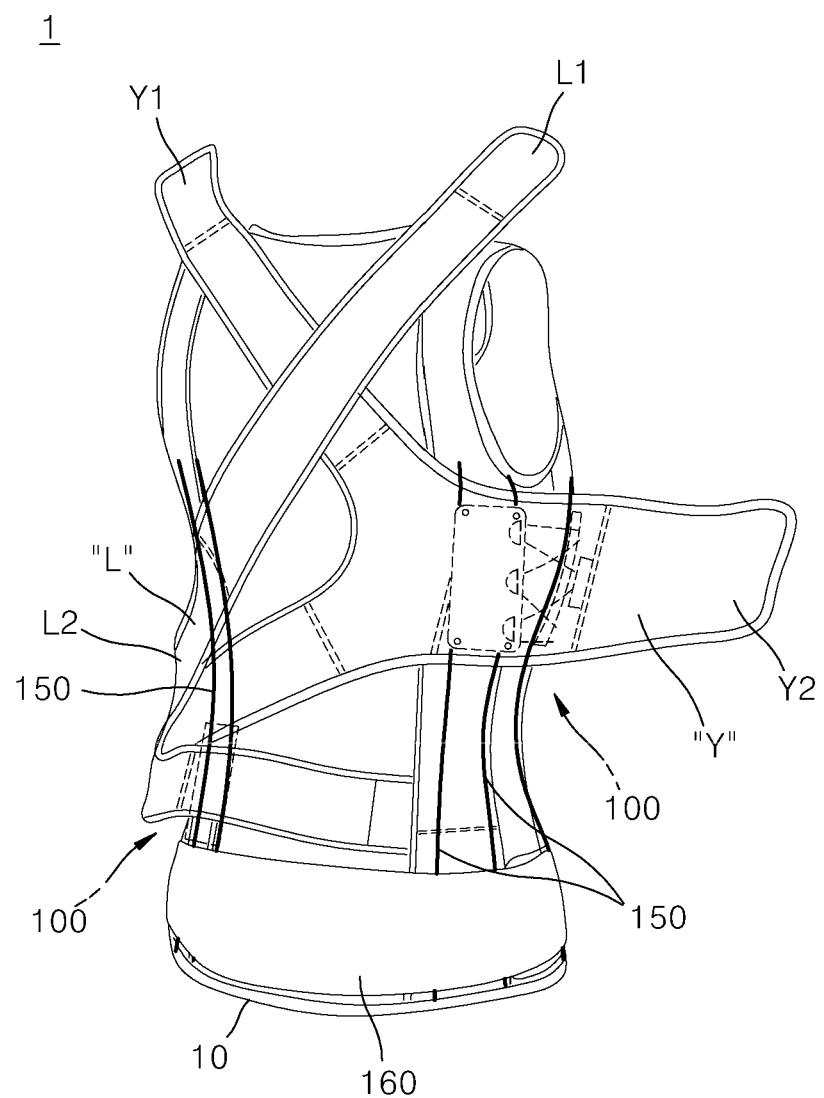
FIG. 2 is a rear perspective view illustrating the wearable device for body correction according to the embodiment of the present disclosure.

FIG. 1 is a front perspective view illustrating a wearable device for body correction according to an embodiment of the present disclosure. FIG. 2 is a rear perspective view illustrating the wearable device for body correction according to the embodiment of the present disclosure.

Referring to FIGS. 1 and 2, the wearable device for body correction, which is designated by reference numeral 1, according to the embodiment of the present disclosure may include an outerwear 10, a curve presser 100a, a strength adjuster 100, and a guide rail 150.

The outerwear 10 may be a top worn on a patient's upper body. The outerwear 10 may be in the form of a vest worn on the patient's upper body. The outerwear 10 may be made of a fabric material. The outerwear 10 may be made of a synthetic fiber.

The curve presser 100a may be disposed on the outerwear 100. The curve presser 100a may press a curve of the body to be corrected. Here, the curve of the body may be a spinal curve. The curve presser 100a may be connected to the strength adjuster 100 through a wire 105.

The curve presser 100a may be largely composed of two parts. That is, the curve presser 100a may be composed of a first part fixed to the outerwear 100, and a second part rotatably coupled to the first part to press the curve in such a manner that it is pulled and rotated by the wire 105.

The strength adjuster 100 may be disposed on the outerwear 10. The strength adjuster 100 may be connected to the curve presser 100a by the wire 105. The strength adjuster 100 may adjust the strength of pressure applied by the curve presser 100a by adjusting the amount of winding/unwinding of the wire 105.

The guide rail 150 may be disposed on the outerwear 10. The guide rail 150 may guide the vertical sliding of the curve presser 100a and the strength adjuster 100. Of course, the guide rail 150 may also guide the vertical sliding of at least one of the curve presser 100a and the strength adjuster 100.

When the guide rail 150 guides the vertical sliding of the curve presser 100a, the position of the curve presser 100a may be adjusted up and down. Therefore, it is possible to correct the curve of the patient by vertically adjusting the position of the curve presser 100a according to the position of the curve.

On the other hand, when the guide rail 150 guides the vertical sliding of the strength adjuster 100, the position of the strength adjuster 100 may be adjusted up and down. Therefore, it is possible to easily adjust the strength of pressure applied by the curve presser 100a by allowing the patient to operate the strength adjuster 100 on his/her own.

The guide rail 150 may move at least one of the curve presser 100a and the strength adjuster 100 from any position to a specific position on the patient's body.

The guide rail 150 may consist of a pair of guide rails 150 configured to guide the vertical sliding of the curve presser 100a, and a pair of guide rails 150 configured to guide the vertical sliding of the strength adjuster 100. However, the guide rail 150 does not necessarily need to consist of the pair of guide rails 150 to guide the vertical sliding of the curve presser 100a, and may be composed of at least one guide rail 150. In addition, the guide rail 150 does not necessarily need to consist of the pair of guide rails 150 to guide the vertical sliding of the strength adjuster 100, and may be composed of at least one guide rail 150.

The curve presser 100a, the strength adjuster 100, and the guide rail 150 may be coupled to the outerwear 10.

The curve presser 100a and the strength adjuster 100 may be disposed on each of the portions of the outerwear 10 corresponding to the respective left and right flanks of the chiropractic patient for correcting the curve of the chiropractic patient due to scoliosis.

Two pairs of guide rails 150 may be placed on the right flank of the outerwear 10 in order to guide the vertical sliding of the curve presser 100a and the strength adjuster 100 located on the right flank of the chiropractic patient.

In addition, two pairs of guide rails 150 may be placed on the left flank of the outerwear 10 in order to guide the vertical sliding of the curve presser 100a and the strength adjuster 100 located on the left flank of the chiropractic patient.

Accordingly, the outerwear 10 may include a total of eight guide rails 150 installed to guide the vertical sliding of the left curve presser 100a and strength adjuster 100 and the vertical sliding of the right curve presser 100a and strength adjuster 100a.

A Y-shaped compression band Y may be installed outside the outerwear 10. The Y-shaped compression band Y may include a first end Y1, a second end Y2, and a third end Y3. The first end Y1 may extend toward the left shoulder in the back of the chiropractic patient. The second end Y2 may extend from the first end Y1 to surround the right waist in the back of the chiropractic patient. The third end Y3 may be branched off from the middle of the first end Y1 and the second end Y2 and extend to surround the left waist in the back of the chiropractic patient.

In addition, an L-shaped compression band L may be installed outside the outerwear 10. The L-shaped compression band L may include a first end L1, a second end L2, and a third end L3. The first end L1 may extend toward the right shoulder in the back of the chiropractic patient. The second end L2 may extend from the first end L1 to surround the left waist in the back of the chiropractic patient. The third end L3 may extend from the second end L2 to surround the back and right waist of the chiropractic patient.

Meanwhile, although not illustrated in detail in the drawings, the curve presser 100a may be disposed so as to press against the chiropractic patient's body corresponding to the curve which is a part required for correction, in order to correct the curve of the chiropractic patient by applying a predetermined correction pressure to the curve.

In more detail, the strength of pressure applied to the chiropractic patient's body by the curve presser 100a may be adjusted when the strength adjuster 100 adjusts the amount of winding/unwinding of the wire 105. In other words, when the strength adjuster 100 winds the wire 105, the curve presser 100a may apply high pressure to the chiropractic patient's body. In contrast, when the strength adjuster 100 unwinds the wire 105, the curve presser 100a may release the pressure applied to the chiropractic patient's body.

The strength adjuster 100 may be provided at a position spaced at a predetermined distance from the curve presser 100a in the circumferential direction of the outerwear 10, so as to adjust the strength of pressure applied to the patient's body by the curve presser 100a connected to the strength adjuster 100 by the wire 105.

The wearable device for body correction 1 according to the embodiment of the present disclosure may further include a pelvic band 160. The pelvic band 160 may be disposed at the lower end of the outerwear 10. The pelvic band 160 may wrap a portion of the outerwear 10 corresponding to the patient's pelvis so as to wrap the patient's pelvis.

The pelvic band 160 may hold the patient's pelvis when the curve presser 100a presses the curve. Thus, the pressure efficiency of the curve presser 100a on the curve can be increased.

A configuration in which the curve presser 100a and the strength adjuster 100 are installed to be slidable vertically on the guide rail 150 will be described in detail below. As described above, the curve presser 100a and the strength adjuster 100 have different functions, but may have a body 110, a support plate 140, and a rail moving block 145, which will be described later, in a common configuration so as to be installed to be slidable vertically on the guide rail 150. However, unlike the strength adjuster 100, the body 110 of the curve presser 100a may not be provided with a dial adjuster 120 and a dial cover 130 to be described later. Only a specific configuration of the strength adjuster 100 will be described below, and a specific description of the curve presser 100a will be omitted.

Figure 3:
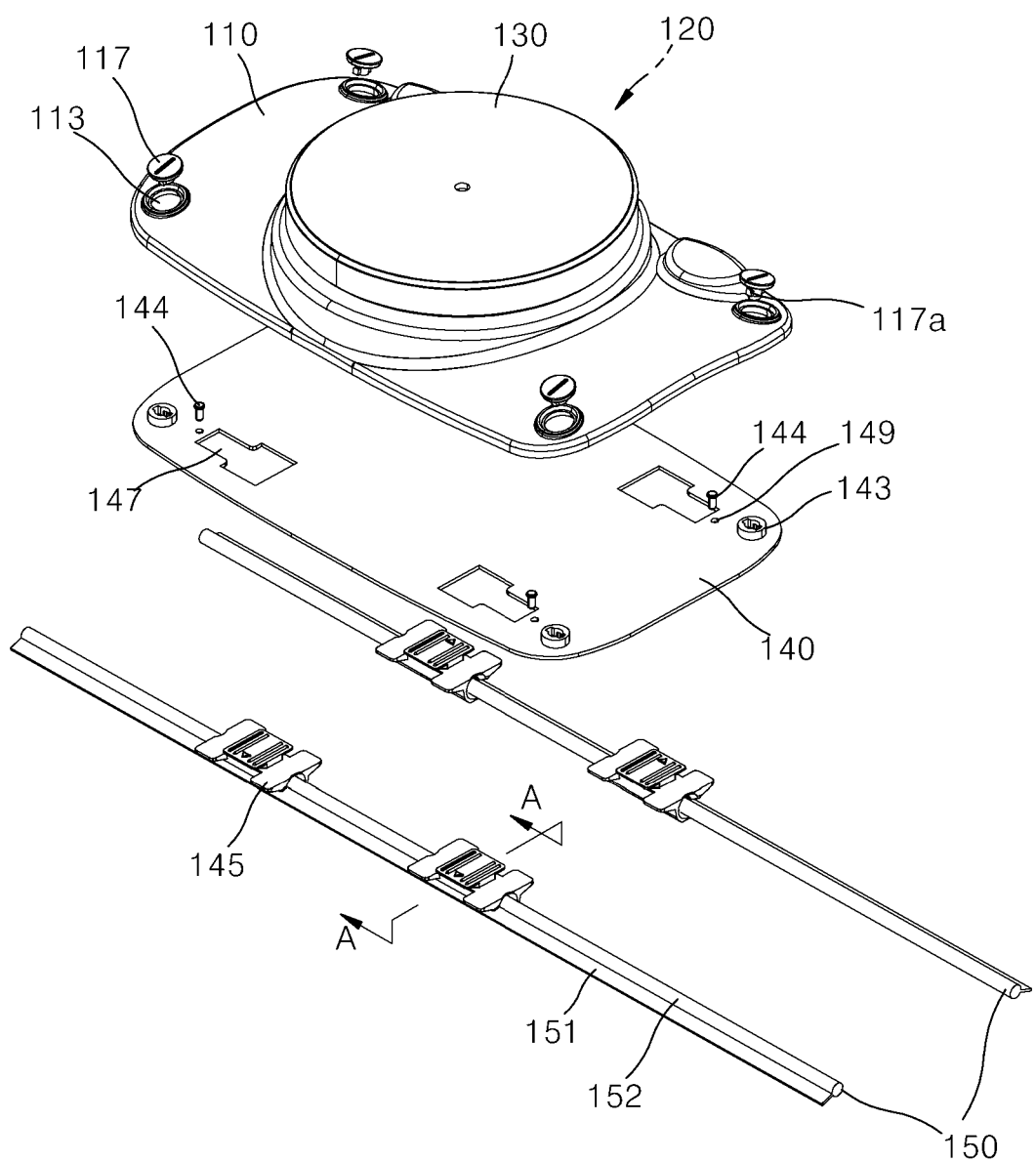
FIG. 3 is an exploded perspective view illustrating an installation structure of the strength adjuster of FIGS. 1 and 2.
Figure 4:
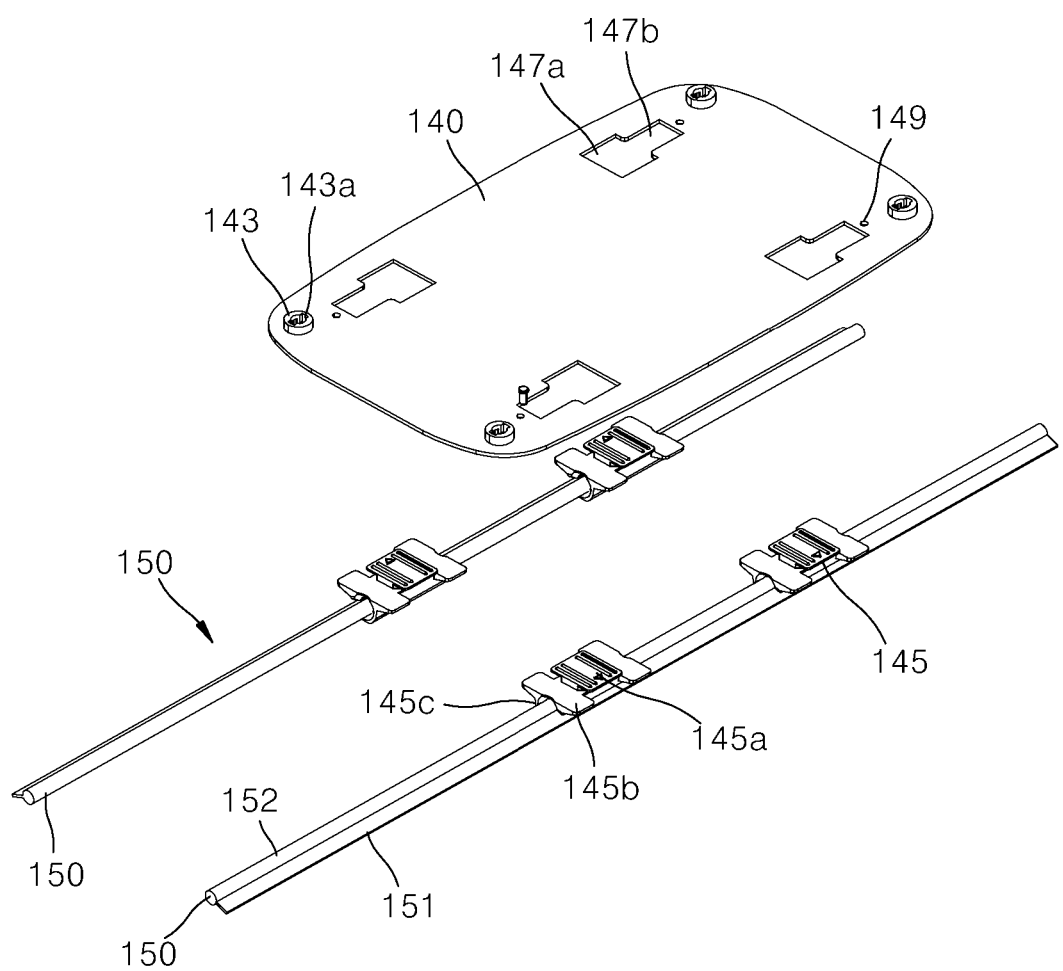
FIG. 4 is an exploded perspective view of FIG. 3 except for the body.
Figure 5:
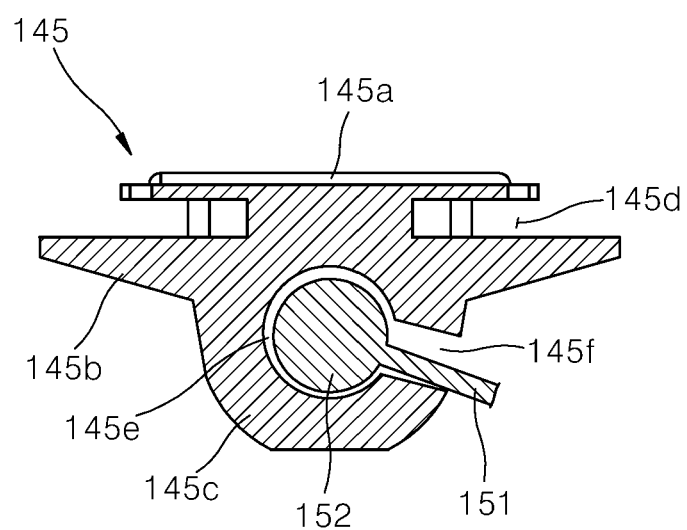
FIG. 5 is a cross-sectional view taken along line A-A of FIG. 3.
Figure 6:
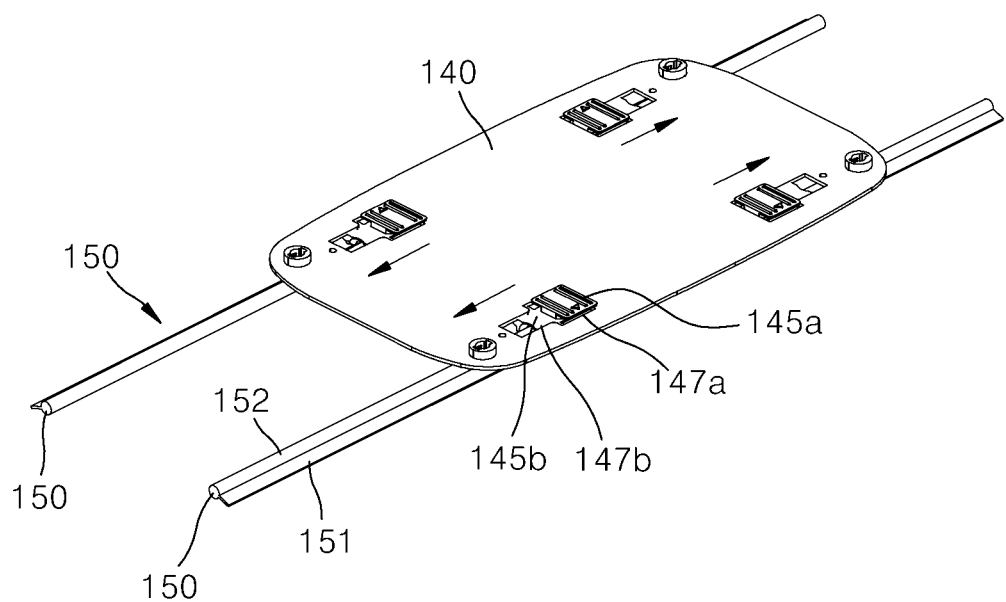
FIGS. 6 and 7 are views illustrating a sequence of coupling the body and the support plate of FIG. 3.
Figure 7:
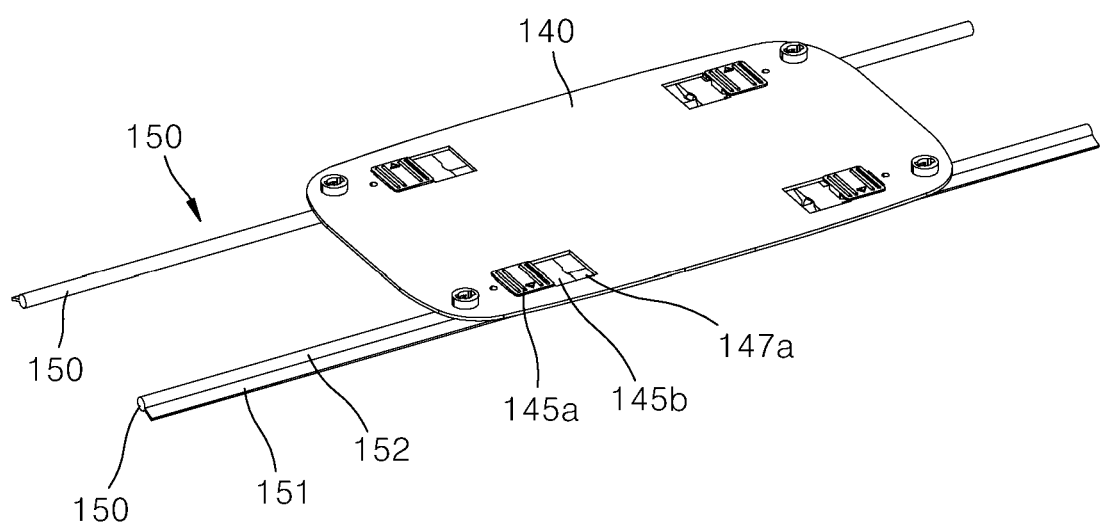

FIG. 3 is an exploded perspective view illustrating an installation structure of the strength adjuster of FIGS. 1 and 2. FIG. 4 is an exploded perspective view of FIG. 3 except for the body. FIG. 5 is a cross-sectional view taken along line A-A of FIG. 3. FIGS. 6 and 7 are views illustrating a sequence of coupling the body and the support plate of FIG. 3.

Referring to FIGS. 3 to 7, the strength adjuster 100 may include a body 110, a support plate 140, and a rail moving block 145.

The body 110 may define the external appearance of the strength adjuster 100. The support plate 140 may be disposed between the body 110 and the guide rail 150. The support plate 140 may be coupled to the body 110. The rail moving block 145 may be coupled to the support plate 140. The rail moving block 145 may be slidably coupled to the support plate 150.

The rail moving block 145 may consist of a pair of rail moving blocks 145 installed for each guide rail 150. The number of rail moving blocks 145 installed on one guide rail 150 may vary, and at least one rail moving block 145 may be installed on one guide rail 150.

The body 110 may be in the form of a plate having a width greater than the separation distance between the pair of guide rails 150. In addition, the body 110 may have an outwardly convex shape as a whole so as to correspond to the body curvature of the chiropractic patient.

The strength adjuster 100 may further include a dial adjuster 120. The dial adjuster 120 may be rotatably coupled to the body 110 to adjust the amount of winding/unwinding of the wire 105.

Although not illustrated in the drawings, the dial adjuster 120 may be rotatably provided on the body 110, and the wire 105 may be wound or unwound around the outer peripheral surface of the dial adjuster 120.

The strength adjuster 100 may further include a dial cover 130 covering the dial adjuster 120. The dial cover 130 may be provided to cover the dial adjuster 120 from the outside, and may rotate the dial adjuster 120 by an operation of rotation to one side or the other side.

The wire 105 extending from the strength adjuster 100 may be connected to one side of the curve presser 100a. When the wire 105 is wound around the outer peripheral surface of the dial adjuster 120 of the strength adjuster 100, the curve presser 100a may press a part of the body to be corrected. On the other hand, when the wire 105 is unwound from the outer peripheral surface of the dial adjuster 120 of the strength adjuster 100, the pressure applied by the curve presser 100a may be released.

The body 110 may be slidably fixed to the pair of guide rails 150 through the support plate 140.

The support plate 140 may be disposed between the body 110 and the pair of guide rails 150. The outer surface of the support plate 140 may come into contact with the inner surface of the body 110, and at least two rail moving blocks 145 may be disposed on the inner surface of the support plate 140 by protruding. The support plate 140 may be slidably coupled to the pair of guide rails 150 through at least two rail moving blocks 145.

The strength adjuster 100 may further include a holder fixing pin 117. The holder fixing pin 117 may couple the body 110 to the support plate 140. The corners of the body 110 may be coupled to the corners of the support plate 140 by a plurality of holder fixing pins 117, respectively.

The body 110 may have a through-hole 113 formed therein. The through-hole 113 may consist of a plurality of through-holes 113 formed at the respective corners of the body 110. The support plate 14 may have a boss 143 inserted into the through-hole 113. The boss 143 may be formed on the outer surface of the support plate 140. The boss 143 may protrude toward the body 110 from the outer surface of the support plate 140 facing the body 110. The support plate 140 may have a square shape corresponding to the body 110, and the boss 143 may consist of a plurality of bosses 143 formed at the respective corners of the support plate 140.

The holder fixing pin 117 may be inserted into the boss 143. In other words, in a state in which the boss 143 is inserted into the through-hole 113 of the body 110, the holder fixing pin 117, excluding the head thereof, may be inserted into a groove formed in the boss 143 from the outside of the body 110. In this state, the head of the holder fixing pin 117 may be latched by the protrusion on the inner wall of the through-hole 113 in the body 110.

The holder fixing pin 117 may have a latching protrusion 117a formed on the outer peripheral surface thereof. The latching protrusion 117a may be formed on the outer peripheral surface of the holder fixing pin 117 that is inserted into the groove formed in the boss 143.

The boss 143 may have a latching groove 143a to which the holder fixing pin 117 is fastened. The latching groove 143a may be formed inside the groove of the boss 143 such that the latching protrusion 117a formed on the outer peripheral surface of the holder fixing pin 117 is latched to the latching groove 143a.

The operator may couple the body 110 and the support plate 140 to each other by inserting the holder fixing pin 117 into the boss 143 and then rotating the holder fixing pin 117 to one side so that the latching protrusion 117a of the holder fixing pin 117 is latched to the latching groove 143a of the boss 143.

Two rail moving blocks 145 may be disposed on one of the pair of guide rails 150 and connected to one side of the support plate 140 in the width direction thereof, and two rail moving blocks 145 may be disposed on the other guide rail 150 and connected to the other side of the support plate 140 in the width direction thereof.

The support plate 140 may have a plurality of mounting holes 147 formed therein. Each of the mounting holes 147 may include a first coupling hole 147a and a second coupling hole 147b. In other words, the first coupling hole 147a and the second coupling hole 147b may be formed in the support plate 140. The second coupling hole 147b may extend in the sliding direction of the rail moving block 145 from the first coupling hole 147a. The second coupling hole 147b may have a smaller width in a direction orthogonal to the sliding direction of the rail moving block 145 than the first coupling hole 147a. The rail moving block 145 may be fitted in the first coupling hole 147a and then slid to the second coupling hole 147b for coupling to the support plate 140.

The rail moving block 145 may include a latching portion 145a, a support portion 145b, and a coupling portion 145c.

The latching portion 145a may have a width in a direction orthogonal to the sliding direction of the rail moving block 145 to be less than or equal to the width of the first coupling hole 147a. The latching portion 145a may have a width in a direction orthogonal to the sliding direction of the rail moving block 145 to be larger than the width of the second coupling hole 147b.

The support portion 145b may have a width in a direction orthogonal to the sliding direction of the rail moving block 145 to be larger than the width of the first coupling hole 147a and the width of the second coupling hole 147b.

Latching grooves 145d may be formed between the locking portion 145a and the supporting portion 145b so that portions at both sides of the second coupling hole 147b in the support plate 140 are inserted into the latching grooves 145d. In other words, when the latching portion 145a of the rail moving block 145 is fitted in the first coupling hole 147a and then slid to the second coupling hole 147b by the operator, the portions at both sides of the second coupling hole 147b in the support plate 140 are latched to the latching groove 145d, with the consequence that the rail moving block 145 may be coupled to the support plate 140.

As such, in the state in which the rail moving block 145 is coupled to the support plate 140, one surface of the latching portion 145a may be in contact with the outer surface of the support plate 140 and one surface of the support portion 145b may be in contact with the inner surface of the support plate 140. Here, the one surface of the latching portion 145a may face the one surface of the support portion 145b. Specifically, the one surface of the latching portion 145a may be an inner surface of the latching portion 145a, and the one surface of the support portion 145b may be an outer surface of the support portion 145b.

The first coupling hole 147a and the second coupling hole 147b may be formed in a plurality of places of the support plate 140. The first coupling hole 147a and the second coupling hole 147b are connected to each other. The length and width of the first coupling hole 147a may be larger than those of the latching portion 145a of the rail moving block 145, and the length and width of the second coupling hole 147b may be smaller than those of the latching portion 145a of the rail moving block 145. Accordingly, the latching portion 145a of the rail moving block 145 may pass through the first coupling hole 147a, but may not pass through the second coupling hole 147b.

In addition, the length and width of the support portion 145b of the rail moving block 145 may be larger than those of the first and second coupling holes 147a and 147b. Accordingly, the support portion 145b of the rail moving block 145 may not pass through both the first coupling hole 147a (which is a relatively large hole) and the second coupling hole 147b (which is a relatively small hole), and may be supported on the inner surface of the support plate 140.

Of course, the latching portion 145a and the support portion 145b of the rail moving block 145 are connected to each other by an interconnection (no reference numeral). Preferably, the interconnection has a smaller length and width than the second coupling hole 147b at least such that the rail moving block 145 is slidable toward the second coupling hole 147b.

Accordingly, in the state in which the latching portion 145a of the rail moving block 145 passes through the first coupling hole 147a of the support plate 140 so that the support portion 145b of the rail moving block 145 is supported on the inner surface of the support plate 140, a fixing pin 144 is fixed through a fixing hole 149 formed in the support plate 140 after the rail moving block 145 is moved toward the second coupling hole 147b. Consequently, the process of coupling the rail moving block 145 to the support plate 140 is completed. In an embodiment of the present disclosure, the first coupling hole 147a and the second coupling hole 147b may be formed in four places of one support plate 140, and each of four rail moving blocks 145 may be coupled to the interconnected first and second coupling holes 147a and 147b.

The coupling portion 145c may protrude from the other surface of the support portion 145b. Here, the other surface of the support portion 145b may be an inner surface of the support portion 145b. The coupling portion 145c may have a guide groove 145e slidably coupled to the guide rail 150.

The guide rail 150 may include an attachment plate 151 and a guide protrusion 152.

The attachment plate 151 may be coupled to the outerwear 110. The attachment plate 151 may be coupled to the outerwear 110 by at least one of sewing and bonding.

The guide protrusion 152 may be formed on one side of the attachment plate 151 in a direction orthogonal to the sliding direction of the rail moving block 145. The guide protrusion 152 may be inserted and rotatably disposed in the guide groove 145e formed in the coupling portion 145c of the rail moving block 145.

The attachment plate 151 may be securely fixed to the outer surface of the outerwear 10 such that the guide protrusion 152 is freely rotatable about the attachment point of the attachment plate 151.

The guide groove 145e formed in the coupling portion 145c of the rail moving block 145 and the guide protrusion 152 formed in the guide rail 150 may have a circular cross section. Thus, when the guide protrusion 152 is inserted into the guide groove 145e so that the rail moving block 145 is vertically slidable on the guide rail 150, the rail moving block 145 may be smoothly slidable up and down.

The coupling portion 145c of the rail moving block 145 may have an opening 145f formed to be open at one side of the guide groove 145e. When the guide protrusion 152 of the guide rail 150 is inserted into the guide groove 145e, the attachment plate 151 of the guide rail 150 may be disposed in the opening 145f.

Since the opening width of the opening 145f is smaller than the diameter of the guide groove 145e, it is possible to prevent the separation of the guide protrusion 152 from the guide groove 145e. In addition, since the opening width of the opening 145f is larger than the thickness of the attachment plate 151, it is possible to smoothly slide the rail moving block 145 up and down.

The diameter of the guide protrusion 152 may be larger than the thickness of the attachment plate 151. The diameter of the guide protrusion 152 may be smaller than that of the guide groove 145e formed in the coupling portion 145c of the rail moving block 145.

The coupling portion 145c of the rail moving block 145 may have an approximately circular shape in section. The inner diameter of the coupling portion 145c is larger than the outer diameter of the guide protrusion 152 of the guide rail 150. Thus, during the vertical sliding of the curve presser 100a or the strength adjuster 100, the rail moving block 145 can be easily slid up and down along the guide protrusion 152 without being latched by the guide protrusion 152.

The wearable device for body correction 1 according to the embodiment of the present disclosure configured as described above is disposed in the outerwear 10 worn by the chiropractic patient on his/her upper body to press a part of the body of the chiropractic patient suffering from scoliosis symptoms. Furthermore, the wearable device for body correction 1 may include at least one of the curve presser 100a and the strength adjuster 100 to be slidable along the guide rail 150 so that the part pressed on the body is changed from one point to a specific point.

However, the wearable device for body correction 1 according to the embodiment of the present disclosure is not necessarily limited to the outerwear 10 worn on the chiropractic patient's upper body, but is applicable to clothing or instruments worn on various parts of the human body. As a result, the wearable device can also be expanded in terms of versatility.

The wearable device for body correction 1 according to the embodiment of the present disclosure is further provided with components for increasing the efficiency of the curve presser 100*a* pressing the body's curve, which will be described below with reference to FIGS. 8 to 10.

Figure 8:
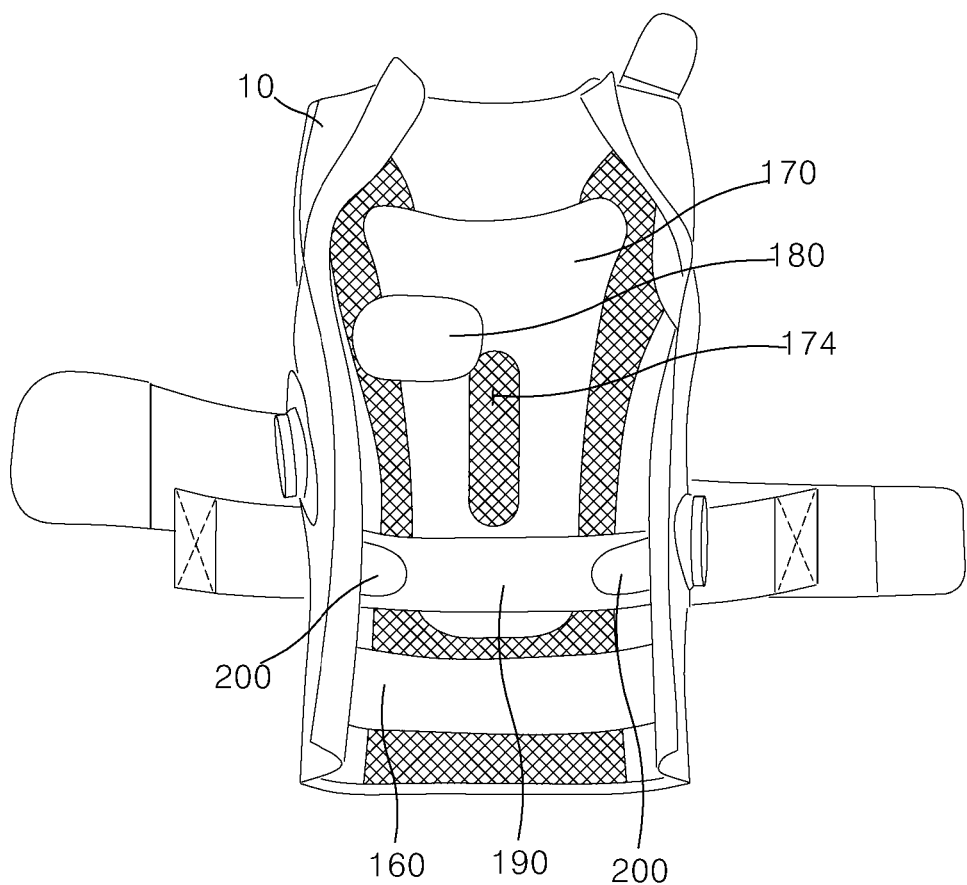
FIG. 8 is a view illustrating an inner surface of the outerwear of FIG. 1.

FIG. 8 is a view illustrating the inner surface of the outerwear of FIG. 1. FIG. 9 is a perspective view illustrating the hump pad of FIG. 8. FIG. 10 is a perspective view illustrating the flank pad of FIG. 8.

Figure 9:
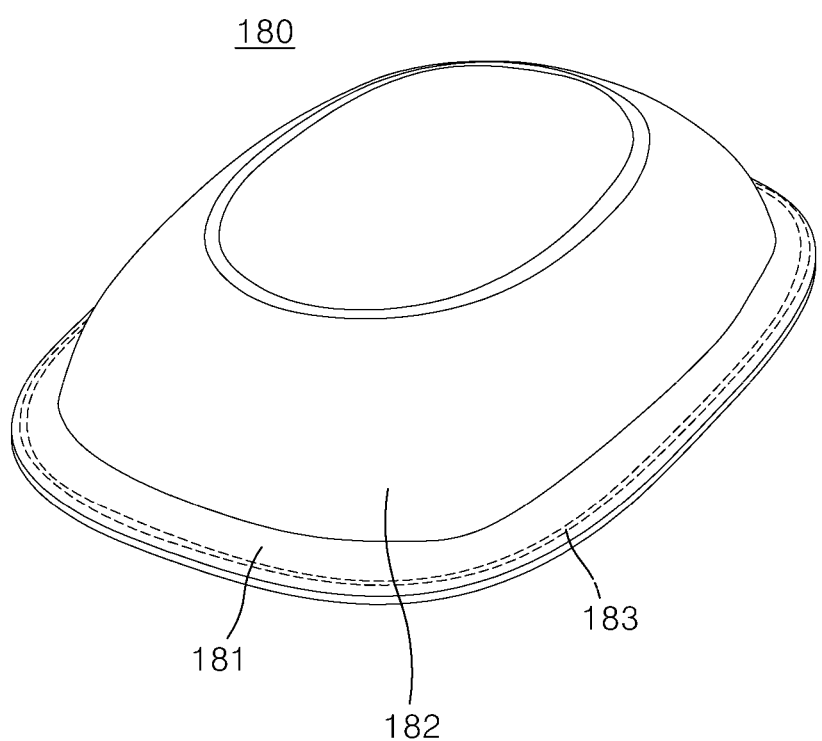
FIG. 9 is a perspective view illustrating the hump pad of FIG. 8.
Figure 10:
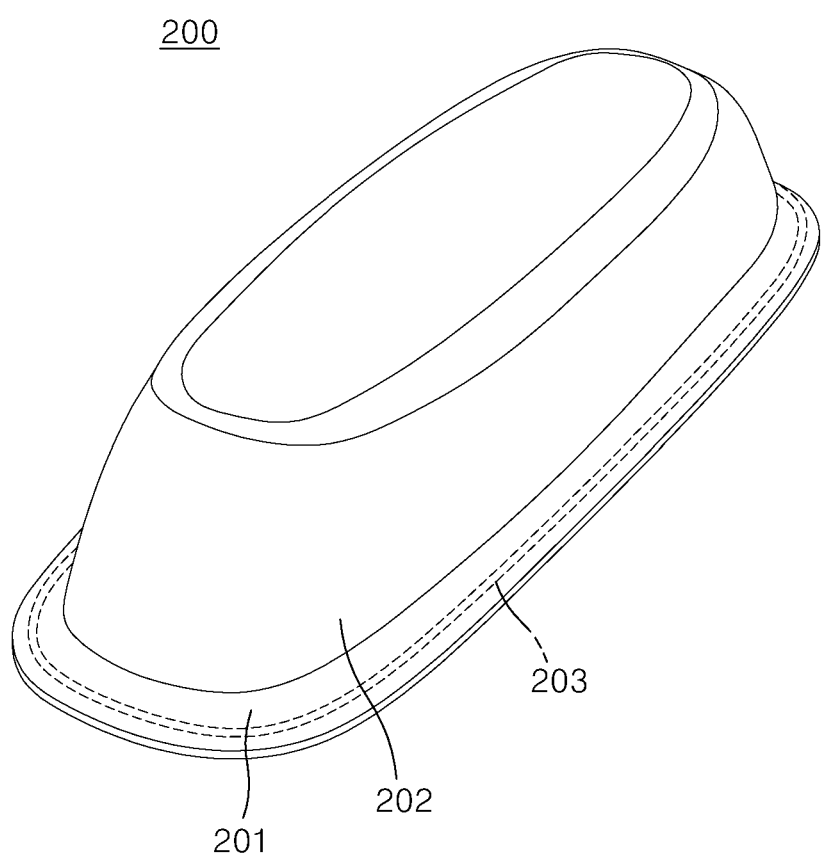
FIG. 10 is a perspective view illustrating the flank pad of FIG. 8.

Referring to FIGS. 8 to 10, the wearable device for body correction 1 according to the embodiment of the present disclosure may include a pelvic band 160, a back reinforcement plate 170, a hump pad 180, flank band 190, and a flank pad 200.

The pelvic band 160 may be disposed at the lower end of the outerwear 10. A portion of the pelvic band 160 may be disposed inside the outerwear 10, and the rest of the pelvic band 160 may be disposed outside the outerwear 10. The pelvic band 160 may wrap a portion of the outerwear 10 corresponding to the patient's pelvis so as to wrap the patient's pelvis. The pelvic band 160 may be made of an elastic material that is capable of elastically pressing the patient's pelvis.

The pelvic band 160 may hold the patient's pelvis when the curve presser 100*a* presses the curve. Thus, the pressure efficiency of the curve presser 100*a* on the curve can be increased.

The back reinforcement plate 170 may be disposed on the inner surface of the back plate of the outerwear 10. The back reinforcement plate 170 is made of a material that is harder than the back plate of the outerwear 10 in order to securely support the patient's back when the curve presser 100*a* presses the curve thereof. Therefore, the efficiency of the curve presser 100*a* pressing the curve can be increased.

The back reinforcement plate 170 may have a vertically elongated opening hole 174 formed therein. The opening hole 174 may be formed in the center between the left and right sides of the back reinforcement plate 170. The opening hole 174 may be formed at a position corresponding to the patient's spine. When the patient wears the wearable device for body correction 1, the patient's curved spine may pass through the opening hole 174 without coming into contact with the back reinforcement plate 170 made of a hard material. Therefore, it is possible to prevent the patient from feeling discomfort due to wearing the wearable device for body correction 1.

The hump pad 180 may be attached to any position of the back reinforcement plate 174 related to the position where the curve presser 100*a* presses the curve, so as to press the hump of the body. Here, the above position may be a position randomly selected by the patient or the doctor.

The hump pad 180 may include a base 181 and a cushion protrusion 182. The base 181 may be in the form of a plate. The base 181 may be attached to the back reinforcement plate 170. The cushion protrusion 182 may protrude from one surface of the base 181. The cushion protrusion 182 may be made of a material having a cushion force to press the human body, and the base 181 may be made of a hard material that is capable of supporting the cushion protrusion 182. The base 181 may have Velcro attached to the other surface thereof, and the hump pad 180 may be attached to any position of the back reinforcement plate 170 through the Velcro.

The base 181 may have a metal wire 183 disposed within the rim thereof. The wire 183 is made of metal. Therefore, when an X-ray is taken after the patient wears the wearable device for body correction 1 with the hump pad 180 attached to the back reinforcement plate 170, the wire 183 may appear white in the taken X-ray. This enables the doctor to easily identify the position and condition of the hump by observing the wire 183 in the taken X-ray.

The flank band 190 may be disposed on the outerwear 10. A portion of the flank band 190 may be disposed inside the outerwear 10, and the rest of the flank band 190 may be disposed outside the outerwear 10. The flank band 190 may wrap a portion of the outerwear 10 corresponding to the patient's flank. The flank band 190 may be made of an elastic material that is capable of elastically pressing the patient's flank.

The flank band 190 may hold the patient's flank when the curve presser 100*a* presses the curve. Thus, the pressure efficiency of the curve presser 100*a* on the curve can be increased.

The flank pad 200 may be attached to any position of the flank band 190 related to the position where the curve presser 100*a* presses the curve, so as to press the human body. Here, the above position may be a position randomly selected by the patient or the doctor.

The flank pad 200 may have the same configuration as the hump pad 180. However, the flank pad 200 may be longer than the hump pad 180. The flank pad 200 differs only in shape from the hump pad 180 and is formed the same configuration, and thus may include a base 201 and a cushion protrusion 202.

The base 201 may be in the form of a plate. The base 201 may be attached to the flank band 190. The cushion protrusion 202 may protrude from one surface of the base 201. The cushion protrusion 202 may be made of a material having a cushion force to press the human body, and the base 201 may be made of a hard material that is capable of supporting the cushion protrusion 202. The base 201 may have Velcro attached to the other surface thereof, and the flank pad 200 may be attached to any position of the flank band 190 through the Velcro.

The base 201 may have a metal wire 203 disposed within the rim thereof. The wire 203 is made of metal. Therefore, when an X-ray is taken after the patient wears the wearable device for body correction 1 with the flank pad 200 attached to the flank band 190, the wire 203 may appear white in the taken X-ray. This enables the doctor to easily identify the positions and conditions of the curve and the hump by observing the wire 203 in the taken X-ray.

As described above, since the metal wires 183 and 203 are disposed inside the hump pad 180 and the flank pad 200, the doctor can easily identify the positions and conditions of the curve and the hump by observing the wires 183 and 203 in the taken X-ray. In order to more specifically identify the positions and conditions of the curve and the hump in the taken X-ray, the wearable device for body correction 1 according to the embodiment of the present disclosure may further include a point band 210 to be described later. Hereinafter, the point band 210 will be described with reference to FIG. 11.

Figure 11:
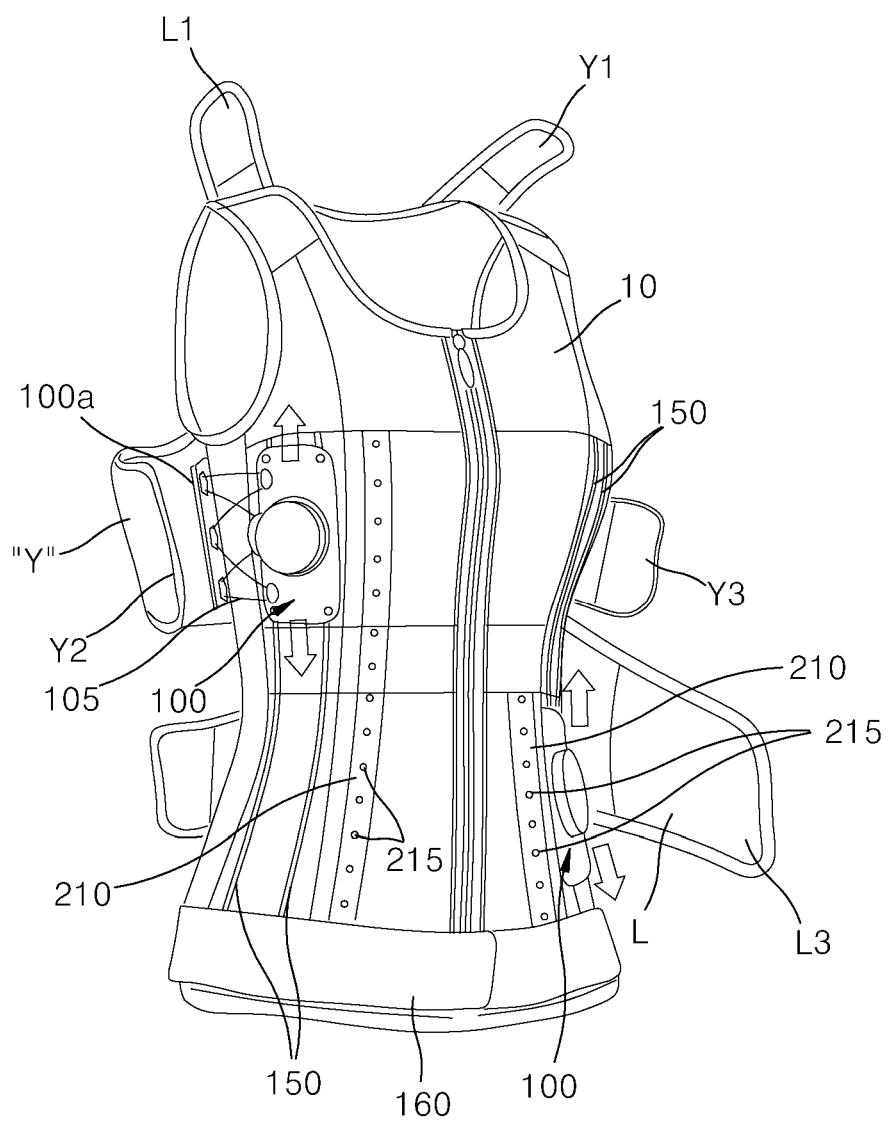
FIG. 11 is a view illustrating a state in which a point band is attached to FIG. 1.

FIG. 11 is a view illustrating a state in which the point band is attached to FIG. 1.

Referring to FIG. 11, the point band 210 may be attached to the outerwear 10. The point band 210 may be attached to any position of the outerwear 10. Here, the above position may be a position randomly selected by the doctor.

The point band 210 may have a plurality of vertically spaced metal points 215 arranged thereon. The metal points 215 are made of metal. Therefore, when an X-ray is taken after the patient wears the wearable device for body correction 1 with the point band 210 attached to the outerwear 10, the metal points 215 may appear white in the taken X-ray. This enables the doctor to easily identify the positions and conditions of the curve and the hump by observing the metal points 215 in the taken X-ray.

As described above, in the wearable device for body correction 1 according to the embodiment of the present disclosure, the position of the curve presser 100a pressing the curve of the body to be corrected is adjustable up and down. Therefore, it is possible to correct the curve of the patient by vertically adjusting the position of the curve presser 100a according to the position of the curve.

In addition, in the wearable device for body correction 1 according to the embodiment of the present disclosure, the position of the strength adjuster 100, which adjusts the strength of pressure applied by the curve presser 100a, is adjustable up and down. Therefore, it is possible to easily adjust the strength of pressure applied by the curve presser 100a by allowing the patient to operate the strength adjuster 100 on his/her own.

In addition, in the wearable device for body correction 1 according to the embodiment of the present disclosure, when the curve presser 100a presses the curve, the pelvic band 160 holds the patient's pelvis. Therefore, it is possible to increase the pressure efficiency of the curve presser 100a on the curve.

In addition, in the wearable device for body correction 1 according to the embodiment of the present disclosure, the hump pad 180 is attached to any position related to the position where the curve presser 100a presses the curve, so that the hump pad 180 presses the hump of the body at the above position when the curve presser 100a presses the curve. Therefore, it is possible to increase the pressure efficiency of the curve presser 100a on the curve.

In addition, in the wearable device for body correction 1 according to the embodiment of the present disclosure, when the curve presser 100a presses the curve, the flank band 190 holds the patient's flank. Therefore, it is possible to increase the pressure efficiency of the curve presser 100a on the curve.

In addition, in the wearable device for body correction 1 according to the embodiment of the present disclosure, the flank pad 200 is attached to any position related to the position where the curve presser 100a presses the curve, so that the flank pad 200 presses the above position when the curve presser 100a presses the curve. Therefore, it is possible to increase the pressure efficiency of the curve presser 100a on the curve.

In addition, in the wearable device for body correction 1 according to the embodiment of the present disclosure, the metal wires 183 and 203 are disposed on the hump pad 180 and the flank pad 200, and the point band 210 has the plurality of metal points 215 arranged thereon. In this case, the metal wires 183 and 203 and the metal points 215 appear in the X-ray taken with the patient wearing the wearable device for body correction 1. Therefore, the doctor can easily treat the positions and conditions of the curve and hump of the patient by observing the wires 183 and 203 and the metal points 215 in the taken X-ray.

Meanwhile, although the wearable device for body correction 1 according to the embodiment of the present disclosure has been described by way of example as being applied to the outerwear 10 worn on the upper body of the chiropractic patient, the present disclosure is not necessarily limited thereto. The wearable device for body correction is also applicable to cervical vertebral clothing worn on the patient's cervical vertebra, lumbar vertebral clothing worn on the patient's lumbar vertebra, arm clothing worn on the patient's arm or hand, and leg clothing worn on the patient's legs or feet.

As is apparent from the above description, in the wearable device for body correction according to the present disclosure, the position of the curve presser pressing the curve of the body to be corrected is adjustable up and down. Therefore, it is possible to correct the curve of the patient by vertically adjusting the position of the curve presser according to the position of the curve.

In addition, in the wearable device for body correction according to the present disclosure, the position of the strength adjuster, which adjusts the strength of pressure applied by the curve presser, is adjustable up and down. Therefore, it is possible to easily adjust the strength of pressure applied by the curve presser by allowing the patient to operate the strength adjuster on his/her own.

In addition, in the wearable device for body correction according to the present disclosure, when the curve presser presses the curve, the pelvic band holds the patient's pelvis. Therefore, it is possible to increase the pressure efficiency of the curve presser on the curve.

In addition, in the wearable device for body correction according to the present disclosure, the hump pad is attached to any position related to the position where the curve presser presses the curve, so that the hump pad presses the hump of the body at the above position when the curve presser presses the curve. Therefore, it is possible to increase the pressure efficiency of the curve presser on the curve.

In addition, in the wearable device for body correction according to the present disclosure, when the curve presser presses the curve, the flank band holds the patient's flank. Therefore, it is possible to increase the pressure efficiency of the curve presser on the curve.

In addition, in the wearable device for body correction according to the present disclosure, the flank pad is attached to any position related to the position where the curve presser presses the curve, so that the flank pad presses the above position when the curve presser presses the curve. Therefore, it is possible to increase the pressure efficiency of the curve presser on the curve.

In addition, in the wearable device for body correction according to the present disclosure, the metal wires are disposed on the hump pad and the flank pad, and the point band has the plurality of metal points arranged thereon. In this case, the metal wires and the metal points appear in the X-ray taken with the patient wearing the wearable device for body correction. Therefore, the doctor can easily treat the positions and conditions of the curve and hump of the patient by observing the wires and the metal points in the taken X-ray.

The present disclosure is not limited to the above effects, and other effects of the present disclosure can be clearly understood by those skilled in the art from description of the appended claims.

It will be understood by those skilled in the art that various modifications may be made without departing from the spirit and scope or essential features of the disclosure. Therefore, it should be understood that the embodiments described above are for purposes of illustration only in all aspects and are not intended to limit the scope of the present disclosure. The scope of the present disclosure is defined by the appended claims, and it should be construed that all modifications or variations derived from the meaning, scope, and equivalent concept of the claims fall within the scope of the disclosure.

What is claimed is:

1. A wearable device for body correction, comprising:
an outerwear worn on an upper body of a patient;
a curve presser disposed on the outerwear and configured to press a curve of the body to be corrected;
a strength adjuster disposed on the outerwear, connected to the curve presser by a wire, and configured to adjust a strength of pressure applied by the curve presser by adjusting an amount of winding/unwinding of the wire; and
a guide rail disposed on the outerwear and configured to guide vertical sliding of at least one of the curve presser and the strength adjuster,
wherein the at least one of the curve presser and the strength adjuster comprises:
a body defining an external appearance thereof;
a support plate disposed between the body and the guide rail and coupled to the body; and
a rail moving block coupled to the support plate and slidably coupled to the guide rail.

2. The wearable device according to claim 1, wherein the strength adjuster further comprises a dial adjuster rotatably coupled to the body to adjust the amount of winding/unwinding of the wire.

3. The wearable device according to claim 1, wherein:
the support plate comprises a first coupling hole and a second coupling hole extending in a sliding direction of the rail moving block from the first coupling hole, the second coupling hole having a smaller width in a direction orthogonal to the sliding direction of the rail moving block than the first coupling hole; and
the rail moving block is fitted in the first coupling hole and then slid to the second coupling hole for coupling to the support plate.

4. The wearable device according to claim 3, wherein the rail moving block comprises:
a latching portion having a width in a direction orthogonal to the sliding direction of the rail moving block to be less than or equal to the width of the first coupling hole and to be larger than the width of the second coupling hole, the latching portion having one surface coming into contact with an outer surface of the support plate;
a support portion having a width in a direction orthogonal to the sliding direction of the rail moving block to be larger than the width of the first coupling hole and the width of the second coupling hole, the support portion having one surface facing the one surface of the latching portion and coming into contact with an inner surface of the support plate; and
a coupling portion protruding from the other surface of the support portion, and having a guide groove slidably coupled to the guide rail.

5. The wearable device according to claim 4, wherein the guide rail comprises:
an attachment plate coupled to the outerwear; and
a guide protrusion formed on one side of the attachment plate in a direction orthogonal to the sliding direction of the rail moving block, and inserted and rotatably disposed in the guide groove.

6. The wearable device according to claim 5, wherein the guide groove and the guide protrusion have a circular cross section.

7. The wearable device according to claim 6, wherein:
the coupling portion has an opening formed to be open at one side of the guide groove; and
the opening has an opening width smaller than the diameter of the guide groove.

8. The wearable device according to claim 1, wherein:
the strength adjuster further comprises a holder fixing pin used to couple the body and the support plate and having a latching protrusion formed on an outer peripheral surface thereof;
the body has a through-hole formed therein;
the support plate has a boss inserted into the through-hole, the holder fixing pin being inserted into the boss; and
the boss has a latching groove formed therein, the latching protrusion being latched to the latching groove.

9. The wearable device according to claim 1, further comprising a point band attached to any position of the outerwear and having a plurality of vertically spaced metal points arranged thereon.

10. The wearable device according to claim 1, further comprising a pelvic band disposed on the outerwear and configured to hold a pelvis of the patient when the curve presser presses the curve.

11. A wearable device for body correction, comprising:
an outerwear worn on an upper body of a patient;
a curve presser disposed on the outerwear and configured to press a curve of the body to be corrected;
a strength adjuster disposed on the outerwear, connected to the curve presser by a wire, and configured to adjust a strength of pressure applied by the curve presser by adjusting an amount of winding/unwinding of the wire; and
a guide rail disposed on the outerwear and configured to guide vertical sliding of at least one of the curve presser and the strength adjuster,
the wearable device further comprising:
a back reinforcement plate disposed on an inner surface of a back plate of the outerwear; and
a hump pad attached to any position of the back reinforcement plate related to a position where the curve presser presses the curve, so as to press the body.

12. The wearable device according to claim 11, further comprising a flank band disposed on the outerwear and configured to hold a flank of the patient when the curve presser presses the curve.

13. The wearable device according to claim 12, further comprising a flank pad attached to any position of the flank band related to a position where the curve presser presses the curve, so as to press the body.

14. The wearable device according to claim 13, wherein each of the hump pad and the flank pad comprises:
a plate-shaped base attached to an associated one of the back reinforcement plate and the flank band;
a cushion protrusion protruding from one surface of the base and having a cushion force to press the body; and
a metal wire disposed within a rim of the base.

* * * * *